United States Patent
Chandra

(10) Patent No.: US 6,390,097 B1
(45) Date of Patent: May 21, 2002

(54) METHOD AND SYSTEM FOR PROVIDING ARTIFICIAL INTELLIGENCE FOR PLANNING AND RISK ASSESSMENT OF SURGICAL PATHS

(75) Inventor: Arun Chandra, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/046,876

(22) Filed: Mar. 24, 1998

(51) Int. Cl.$^7$ .............................................. A61B 19/00
(52) U.S. Cl. ..................................................... 128/898
(58) Field of Search ................................ 128/897, 898; 606/1; 364/130

(56) References Cited

U.S. PATENT DOCUMENTS

| | | | |
|---|---|---|---|
| 5,343,385 A | 8/1994 | Joskowicz et al. | 364/167.01 |
| 5,402,801 A | 4/1995 | Taylor | 128/989 |
| 5,445,166 A | 8/1995 | Taylor | 128/897 |
| 5,572,999 A | 11/1996 | Funda et al. | 128/653.1 |

*Primary Examiner*—Mickey Yu
*Assistant Examiner*—Dinh X. Nguyen
(74) *Attorney, Agent, or Firm*—Casimer K. Salys; Bracewell & Patterson, L.L.P.

(57) ABSTRACT

A method and system for providing artificial intelligence for planning and risk assessment of surgical paths to a tumor in an organ. The method and system achieve their objects related to path planning by providing a data-processing system programmed to do at least the following: define one or more risk-of-damage probability spaces within an organ, and, utilizing the defined risk-of-damage probability spaces, calculate an optimum path to the tumor in the organ. The definition of the risk-of-damage probability spaces can be done as follows: at least one functional region within an organ is defined; the defined functional region is subdivided into subregions; and a risk-of-damage probability is associated with each of the subregions such that a higher probability indicates a concomitant loss of function of the at least one functional area within the organ. The method and system achieve their objects related to risk assessment by providing a data-processing system programmed to do at least the following: define one or more risk-of-damage probability spaces within an organ; receive an input of a location, relative to the organ, of a surgical instrument; receive an input of a location of a tumor within the organ; define moves relative to paths, defined by specified path perspectives, from the location of the surgical instrument to the tumor within the organ; assess risks for the defined moves relative to the paths defined by specified path perspectives; and indicate the risks associated with the moves relative to the paths defined by specified path perspectives.

28 Claims, 12 Drawing Sheets

METHOD AND SYSTEM FOR PROVIDING ARTIFICIAL INTELLIGENCE FOR PLANNING AND RISK ASSESSMENT OF SURGICAL PATHS

BACKGROUND OF THE INVENTION

1. Field of the Invention

The present invention relates, in general, to a method and system for planning surgical paths and associating risks with planned surgical paths. In particular, the present invention relates to a method and system for planning surgical paths and associating risks with planned surgical paths, wherein the surgical paths are those paths leading to a neurological tumor, such as a brain tumor.

2. Description of Related Art

Anatomically, the brain consists of three main structures: the central brain stem, the cerebrum, and the cerebellum. Each such structure contains within it many other defined regions and/or substructures associated with specific brain function(s).

The brain stem is divided into substructures. Such substructures include the thalamus, hypothalamus, and medulla oblongata. The thalamus is the relay station for incoming sensory signals and outgoing motor signals passing to and from the brain stem and cerebrum. The hypothalamus regulates or is involved directly in the control of eating, drinking, temperature regulation, sleep, emotional behavior, sexual activity, and visceral functions. The medulla oblongata regulates and controls cardiac, vasoconstrictor, and respiratory functions, as well as other reflex activities, including vomiting.

The cerebrum is the largest part of the human brain and is divided into several substructures. These substructures include, among others, the right and left cerebral hemispheres, each of which is divided by fissures and gyri (convolutions) into five lobes: the frontal, parietal, temporal, occipital, and insula lobes.

Many distinct brain functions have been associated with different regions and substructures within the cerebrum. These regions and substructures include the following. The somatomotor area, located just in front of what is known as the central fissure of one cerebral hemisphere, is responsible for nearly all voluntary movement of body muscles. The somatosensory area, which is responsible for touch and taste, which is located just behind what is known as the central fissure of one cerebral hemisphere. The region of the cortex responsible for hearing is located in the upper, or superior, convolution of the temporal lobe of one cerebral hemisphere. The visual cortex, the region responsible for seeing, is located in the occipital lobe of one cerebral hemisphere. The olfactory area, the region responsible for smell, is located in the front, internal portion of the temporal lobe. Broca's area responsible for the muscle movements of the throat and mouth used in speaking, is located just beneath the motor area. The understanding of speech and reading has been associated with areas between the auditory and visual areas. The frontal area of the human cortex is responsible for awareness, intelligence, and memory.

The cerebellum is essential to the control of movement of the human body in space. It acts as a reflex center for the coordination and precise maintenance of equilibrium. Voluntary muscle tone—as related to posture, balance, and equilibrium—is similarly controlled by the cerebellum. All motor activity depends on the cerebellum.

The foregoing identified functional areas are just a fraction of those areas of the brain with which a specific function has been associated. Eloquence can be defined to be the quality of forceful or persuasive expressiveness. Consequently, areas of the brain identified with the expression of functions will be referred to herein as eloquent areas. Damage to "eloquent" areas of the brain typically results in severe impairment or elimination of the function(s) associated with such damaged eloquent area (e.g., severe damage to the medulla oblongata structure usually results in immediate death).

A brain tumor is an abnormal growth, swelling, or enlargement in the brain. There are many types of brain tumors such as those arising from the brain itself (e.g., astrocytoma, glioblastoma, oligodendroglioma, ependymoma), those arising from the brains coverings, or meninges, (e.g., meningiomas, pituitary tumors, pineal tumors), or those arising from nerves at the base of the brain (e.g., acoustic neuromas, schwannomas), and even tumors arising from outside the brain (metastatic brain tumors). This last case occurs when cancer cells travel through the bloodstream and lodge in the brain.

Brain tumors can be malignant or benign. A malignant tumor is one that is actively destroying surrounding brain cells. A benign tumor is a mass or swelling that is growing, but is not destroying the surrounding brain cells. While a benign tumor in other organs is not ordinarily cause for alarm, a benign brain tumor is cause for alarm.

The brain is encased in the cranium. The cranium is a dome-like vault of bone and cartilage that is essentially unyielding. Surrounding the brain is cerebrospinal fluid under a pressure, which supports the brain and protects it from injury. Cerebrospinal fluid is essentially incompressible, and thus the introduction of a tumor, even a benign one, into the cranial vault will require compression of the structures which can be compressed: the cells of the brain. Such compression ultimately will result in brain injury, and thus even benign tumors must be removed as quickly as possible. Thus, even a benign tumor can cause severe damage and must be removed quickly and in its entirety. Thus, irrespective of whether a brain tumor is malignant or benign, an active course of treatment must be engaged in to remove the tumor.

Unfortunately, this is easier proposed than done, for brain tumors are significantly different from other types of tumors, and hence are uniquely difficult to remove. There are several reasons for this, but perhaps the most significant is that brain tumors are in/on the brain, and thus reaching and removing the tumor with surgical instruments gives rise to the risk that eloquent brain areas will be damaged in either the process of reaching the tumor or removing it. A second reason is that brain tumors aren't like ordinary tumors: brain tumors are polyclonal, which means that what appears to be one tumor is actually many (sometimes over a thousand) tumor clones colocated in one area. Consequently, true tumor margins do not exist and consequently total removal by local therapy (surgery, radiation, heat, cold, etc.) is not possible. A third reason is that the brain is separated from the blood-stream by the blood-brain barrier, and consequently many blood-born chemotherapeutic agents cannot reach the brain via the blood-stream. A fourth reason is that many brain tumor cells live in a low oxygen (hypoxic) environment, and it has been found empirically that these hypoxic cells are: (1) radio-resistant; (2) often chemotherapy resistant; and (3) far from the blood supply. Thus, brain tumors prove to be exceedingly difficult to treat as compared with other tumors, as the following simple example will make clear.

Imagine that a particular tumor weighs about 100 grams. Consider the following: 100 gm of tumor typically has approximately 100 billion cells. Because a typical tumor can double in size and volume in a matter of weeks, from a course of treatment standpoint it makes sense to decrease the size of the mass of the tumor right away. Surgery is the preferred way of radically reducing the volume of a tumor, removing anywhere from 80 to 90% of the tumor mass. Recent advances in surgical technologies have aided in the removal of brain tumor tissue with a newer, higher net percentage tumor reduction of 90–99%. These include computer assisted stereotactic surgery, laser instrumentation (carbon dioxide, argon, and Yag), ultrasonic aspiration, operative phototherapy, focused beam radiotherapy proton beam radiation—the Gamma knife, linear accelerator—the "X-knife," brachytherapy—radiation seeds implanted into the tumor bed, cryotherapy, thermal therapy, ultrasonic therapy, phototherapy, drug and immunotherapies injected locally into the tumor bed via an Omaya reservoir, intraarterial therapy—selective exposure of involved brain via angiography.

The foregoing percentage removals sound good until one considers the following: 90% removal of tumor (100,000,000,000 cells), leaves 10 billion cells. Even if one assumes a 99% removal of tumor (100,000,000,000 cells), this still leaves 1 billion cancer cells in the brain.

Thus, no matter how good the local surgical therapy is, in the foregoing simple example it is clear that the patient is still left with at least 1 billion tumor cells.

Consequently, brain tumor treatment typically consists of following up the surgical therapy with radiotherapy and/or chemotherapy. Thus, any given course of treatment of brain tumors usually involves, at a minimum, some form of surgical intervention, plus some form of chemical therapy, plus some form of radiation therapy. There are significant risks associated with each form of treatment, as well as with the course of treatment considered as a whole.

With respect to surgical intervention, one of the most significant risks is that of damage to the above-described eloquent brain areas. These risks are often closely related to the path taken by the surgical instruments from the outside of the cranium to the tumor within the brain, the location, the size of the tumor at the time of surgery, and the percentage of the tumor that is ultimately removed. For example, one path to a tumor might have associated with it the risk of damage to the brain centers controlling feeling in one area of the body, while another path might have the risk damage to the brain centers wherein are contained the patient's individual identity. Alternatively, one path might have associated with it a risk of loss to a major eloquent area, while another path might have associated with it damage associated with a number of more minor surgical areas.

With respect to radiation therapy, it is known that the dosage needed to cure all malignant brain tumors is approximately 12,000 Rads. However, such a high dosage is also extremely neurotoxic and therefore deadly. Consequently, the medical community consensus is that radiation doses of 5,000 to 6,000 rads is the standard of care that should be provided by the reasonably prudent practitioner in this area. These doses have "acceptable" brain toxicity rates. Unfortunately, only the very, very rare tumor is adequately treated with this radiation dosage. Also, different types of cells have more or less susceptibility to radiation therapy (e.g., hypoxic cells being relatively less sensitive to radiation). Thus, a significant risk associated with radiotherapy is the risk that the tumor will not respond. Furthermore, if the radiotherapy is via a directed beam of radiation, such radiation will tend to kill everything in the beam's path, so risks of damage similar to those associated with a surgical path are also associated with the radioactive path.

With respect to chemotherapy, an extraordinary compendium of chemotherapeutic agents is under constant development at present, but as has been discussed, such agents have limited use due to the blood-brain barrier, and thus one risk associated with chemotherapy is the risk of not reaching the tumor. Another risk is that such therapies themselves tend to make the patient very sick, oftentimes wiping out the immune system of the patient in to course of killing the tumor.

Furthermore, selectivity (killing tumor cells while sparing healthy cells) is also a risk with chemotherapy. It is possible to surgically place such chemotherapeutic agents, but such placement moves one right back into the risks associated with therapy.

As has been discussed, a given course of treatment for a brain tumor has associated with it typically at least three major components: surgery, radiation, and chemotherapy. Furthermore, as has been discussed, each component associated with a given course of treatment has associated with it several risk factors. Consequently, the risks and prognoses associated with a given course of medical treatment are dependent upon the individual risks associated with each component of the treatment.

Thus, possible courses of medical treatments of brain tumors have associated with them a dizzying array of variables, such as, to name just a few, the possible surgical paths to be taken to the tumor and the risks associated with same, the possible radiation paths to be traveled to the tumor and the risks associated with same, and the effectiveness of various radiation and chemotherapy associated with the tumor type and its locations, as well as side effects associated with such radiation therapy and chemotherapy.

Current practice is for the medical personnel (e.g., surgeons, oncologists, hematologists, etc.) to meet with the patient and outline various courses of treatments and possible risks and prognoses associated with such courses of treatment. Typically, this assessment is broken down into pre-surgical and post-surgical phases. In the pre-surgical phase, the risks and prognoses are basically done in an idealized text-book type setting. In the post-surgical phase, the risks and prognoses are done with respect to what actually occurred during surgery, as well as what was actually found during surgery related to the location, size, composition, and percentage of the actual tumor removed during the surgery.

Even in the rather abstract discussion set forth above, it is clear that there are a dizzying array of variables, spanning several disjoint medical subspecialities, associated with tumor treatments. Consequently, the current practice involved in the choice of a given course of treatment is intuitive more than anything else, in that each medical professional involved sets forth his perspective of the risks and benefits associated with different phases of particular courses of treatments, and then the lead surgeon in conjunction with the patient chooses a given course of treatment, more typically by intuition and back of the envelope informal calculations than by anything else.

It is undeniable that intuition plays a large and indispensable part medical treatment. However, there are instances where the exercise of such intuition is appropriate and instances where it is not. Such intuition is appropriate where a decision process truly can't be quantified and the choice to be made resolves to a manner of human judgement, such as a choice among given medical treatments when all the variables are known. However, such intuition is inappropriate where virtually all variables involved can be quantified, but the number and possible permutations of those variables exceeds the ability of the human brain to practicably process them.

Given the fact that the majority of factors associated with brain tumors can be quantified, it is apparent that a need exists for a method and system which will allow the quick and efficient assessment of the various risks and prognoses associated with various courses of medical treatment of brain tumors, especially when such courses of treatment span/encompass many different and varied medical subspecialties.

In particular, one very significant risk is that associated with various planned surgical paths to a tumor. Furthermore, in light of the fact that a surgeon must often make mid-surgery corrections to a planned path due to unforseen complications, another very significant risk is that associated with a surgeon being forced to take a surgical path which he did not originally plan to take.

It is therefore apparent that a need exists for a method and system which will provide artificial intelligences capable of assisting with surgical planning, in both a presurgical and real-time surgical context.

SUMMARY OF THE INVENTION

It is therefore one object of the present invention to provide a method and system for planning surgical paths and associating risks with planned surgical paths.

It is therefore another object of the present invention to provide a method and system for planning surgical paths and associating risks with planned surgical paths wherein the surgical paths are those paths leading to a neurological tumor, such as a brain tumor.

The method and system achieve their objects related to path planning by providing a data-processing system programmed to do at least the following: define one or more risk-of-damage probability spaces within an organ, and, utilizing the defined risk-of-damage probability spaces, calculate an optimum path to the tumor in the organ. The definition of the one or more risk-of-damage probability spaces can be done as follows: at least one functional region within an organ is defined; the defined at least one functional region is subdivided into one or more subregions; and a risk-of-damage probability is associated with each of the one or more subregions such that a higher probability indicates a concomitant loss of function of the at least one functional area within the organ. The method and system achieve their objects related to risk assessment by providing a data-processing system programmed to do at least the following: define one or more risk-of-damage probability spaces within an organ; receive an input of a location, relative to the organ, of a surgical instrument; receive an input of a location of a tumor within the organ; define one or more moves relative to one or more paths, defined by one or more specified path perspectives, from the location of the surgical instrument to the tumor within the organ; assess one or more risks for the defined one or more moves relative to the one or more paths defined by one or more specified path perspectives; and indicate the risks associated with the one or more moves relative to the one or more paths defined by one or more specified path perspectives.

The above-as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF THE INVENTION

The following describes several artificially intelligent tools useful in the medical treatment of brain tumors, especially when such treatment involves neurosurgery. As used herein, the term artificially intelligent means simulation by a computer system of functions that are normally associated with human intelligence, such as a computer system programmed (by hardware, software, firmware, etc.) to perform functions that are normally associated with human intelligence; furthermore, as used herein the term artificially intelligent, and analogues thereof, also include expert systems, which are computational systems that provide for solving problems in a particular application area by drawing inferences from a knowledge base (a computer database that contains information about human experience in a particular field of knowledge and data resulting from solution of problems that have been encountered) by utilizing a computer system programmed to process information pertaining to a particular application. *IBM Dictionary of Computing* 32–33, 252, 372 (10th ed. 1994). As will be described below, these tools can be used during presurgery planning, surgery itself, and post-surgery prognosis. These tools will be described in the contexts of methods and systems, which provide machine intelligences capable of accepting multiple inputs, both directly and peripherally, related to the medical course of a brain tumor treatment, and furthermore capable of providing multiple risk assessments and prognoses based upon such inputs; further described will be a neurosurgery navigation tool which can be used in a static pre-surgery planning context, and another neurosurgery navigation tool which can be used in near-real-time, during an actual brain surgery, to help a surgeon select a context-dependent least risky path to a tumor. Those skilled in the art will recognize that while the present inventions are being described in the context of medical treatments specifically involving brain/neurosurgery, the tools described herein can be applied to virtually any course of medical treatment involving risks and prognoses.

The intelligent neurosurgery framework provides services during presurgery, surgery, and postsurgery phases. In what follows the basic principles of this framework will be described.

Overall Framework

Figure 1:
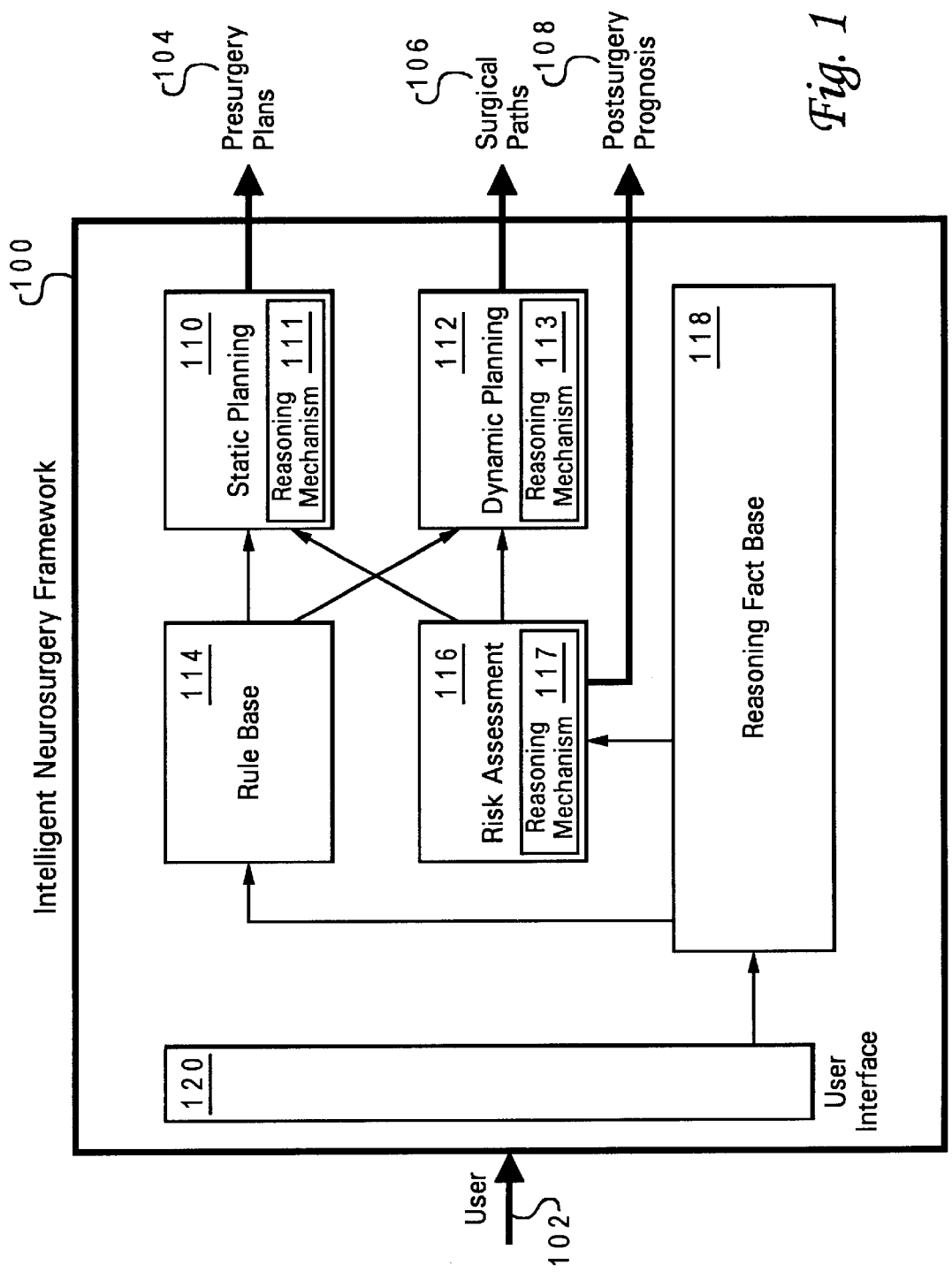
FIG. 1 shows an overall intelligent neurosurgery framework.

Refer now to FIG. 1. FIG. 1 shows an overall intelligent neurosurgery framework 100. The user (which can be a human user or a machine user, such as a computer supplying the input) inputs data 102 into this framework. The outputs from framework 100 are presurgical plans 104, surgical paths 106, and postsurgery prognosis 108. The major components of the framework shown in FIG. 1 are Static Planning Mechanism 110, Dynamic Planning Mechanism 112, Rule Base 114, Risk Assessment Mechanism 116, Reasoning Fact Base 118, and User Interface 120. Static planning mechanism 110 coordinates with risk assessment mechanism 116 and rule base 114 and is used during presurgery planning. During presurgery planning, this tool (static planning mechanism 110) can be used to both assess the risk of surgery, and also to find the least risky or optimum path to the tumor. Dynamic planning mechanism 112 coordinates with risk assessment mechanism 116 and rule base 114 and is used during surgery. During surgery this mechanism (dynamic planning mechanism 112) can be used to provide real-time risk assessment. This risk assessment can be used with existing neurosurgery guidance systems to reduce the risk involved with neurosurgery. Rule base 114 has inbuilt rules to guide static planning reasoning mechanism 111, dynamic planning reasoning mechanism 113, and risk assessment reasoning mechanism 117, included within static planning mechanism 110, dynamic planning mechanism 112, and risk assessment mechanism 116 respectively, intelligently. Risk assessment mechanism 116 uses probability spaces, in the fashion described below, derived from brain maps obtained by techniques such as functional MRIs. Risk assessment mechanism 116 can also be used for post surgery assessment of the prognosis and also for providing recommendations. Reasoning fact base 118 contains the various variables used to reason with. The tool uses the variables with inbuilt rules to reason intelligently. User interface 102 is used to communicate with the user. In one embodiment, one or more component parts of frame work 100 are to be embedded in a neurosurgery guidance system, and in such embodiment user interface 120 will merely amount to communications between program entities, as is well understood by those in the art, and in such embodiment user interface 120 is expected to be developed by the overall neurosurgery guidance system. In another embodiment, user interface 120 is implemented by means of standard computer entry mechanisms, such as keyboard entry, touch screen entry, voice recognition systems, etc.

Risk Assessment Factors Utilized in Overall Framework

Reasoning factors (a.k.a. risk assessment factors obtained from reasoning fact base 118) are used by risk assessment mechanism 116 for uncertainty reasoning to calculate the risk of neurosurgery during presurgical planning, surgery, or post surgery prognosis. The following risk factors are used for uncertainty reasoning: tumor type, tumor size, tumor removal percentage, total path, eloquence removal percentage, eloquent path, closeness to eloquence, surgery time, chemotherapy factor, radiotherapy factor, radiation factor, patient age, neurosurgeon experience, medical staff skill, medical facility. The tumor type risk factor is a risk factor associated with the type and grade of a tumor (astrocytoma, glioblastoma). The tumor size risk factor is a risk factor associated with the size of a tumor. The tumor removal percentage risk factor is a risk factor associated with the percentage of the tumor that can/will be removed. The total path risk factor is determined, after a good path is found by the static planning mechanism 110, by associating a risk factor with the total surgical path. The eloquence removal percentage risk factor is a risk factor associated with the percentage of an eloquent area that has to, or will, be removed. The eloquent path risk factor is a risk factor that is associated with the fact that a surgical path through an eloquent region cannot be avoided. The closeness to eloquence risk factor is risk factor that is associated with a path's closeness to eloquent regions, after such a path has been found by a planning mechanism. The surgery time risk factor is a risk factor associated with the total estimated surgery time. The chemotherapy risk factor is a risk factor associated with a given tumor's predicted non-responsiveness to chemotherapy. The radiotherapy risk factor is a risk factor associated with a given tumor's non-responsiveness to radiotherapy. The radiation risk factor is a risk factor associated with a given tumor's non-responsiveness to radiation. The patient age risk factor is a risk factor associated with a given patient's age. The neurosurgeon experience risk factor is risk factor associated with a neurosurgeon's inexperience either from a global perspective or with respect to a given procedure. The medical staff skill risk factor is a risk factor associated with medical staff skills. The medical facility risk factor is a risk factor associated with the goodness of the medical facility.

Risk Assessment Reasoning Utilized by Overall Framework

Risk assessment reasoning is engaged in by static planning reasoning mechanism 111, dynamic planning reasoning mechanism 113, and risk assessment reasoning mechanism 117, included within static planning mechanism 110, dynamic planning mechanism 112, and risk assessment mechanism 116 to determine various and sundry numeric risks. The numeric risk associated with presurgery operations, surgery operations, and post surgery prognosis are based on the 15 risk variables described above.

In one embodiment, the risk variables are partitioned into two groups of risk variables: (1) Peripheral Variables, and (2) Path Variables. In a general sense, peripheral variables relate to those factors which make up the totality of the "environment" in which a given medical procedure is performed, while path variables constitute, in the main, those variables which can be directly associated with specific factors directly related to a given course of medical treatment. Specifically, in one embodiment the aggregate risk factor associated with the peripheral variables is based on the rules in the rule base. In this embodiment, the peripheral variables are deemed to be tumor type, tumor size, chemotherapy factor, radiotherapy factor, radiation factor, neurosurgeon experience, medical facility, medical staff skill, and patient age. The risk factor score associated with each of these variables can be one of: 0, 10, 20, 50, 100. The assignment of these scores is based on the rule base which is built in conjunction with medical experts. As an example, if a patients age is 42 a risk score of 50 is assigned. The building of this rule base in conjunction with medical experts can be achieved via standard knowledge engineering techniques well known to those within the art. The aggregate risk factor associated with the path variables is based on the planning surgical paths algorithm shown below. In one embodiment, the path variables are deemed to be tumor removal factor, total path, eloquent path, closeness to eloquence, eloquent removal factor, and surgery time. The risk factor score associated with each of these variables can be one of: 0, 10, 20, 50, 100. The assignment of these scores is based on the planning surgical paths algorithm. Some of the data to this algorithm is provided by medical experts and incorporated via knowledge engineering techniques well known to those within the art.

In yet another embodiment, both the peripheral and path variables are further subdivided into three groups. These groups are (1) Presurgery Risk Group, (2) Surgical Operation Risk Group, and (3) Post Surgery Risk Group.

In the Presurgery Risk Group the peripheral variables used to calculate the presurgery risk are tumor type, tumor size, neurosurgeon experience, medical facility, medical staff skill, and patient age. All these variables have a weight of 1. As a result the peripheral variables can contribute anywhere between 0 and 600 towards the presurgery risk. All the path variables are used to calculate the presurgery risk. Tumor removal factor, total path, and surgery time have a weight of 2. Eloquent path, and closeness to eloquence have a weight of 3. Eloquent removal factor has a weight of 4. These weights can be adjusted in conjunction with medical experts. Path variables can contribute from 0 to 1600 towards the presurgery risk. The total presurgery risk score can vary from 0 to 2200.

In the Surgical Operation Risk Group the peripheral variables used to calculate the surgical operation risk are tumor type, tumor size, neurosurgeon experience, medical facility, medical staff skill, and patient age. All these variables have a weight of 1. As a result the peripheral variables can contribute anywhere between 0 and 600 towards the surgical operation risk. All the path variables are used to calculate the surgical operation risk. Tumor removal factor, total path, and surgery time have a weight of 2. Eloquent path, and closeness to eloquence have a weight of 3. Eloquent removal factor has a weight of 4. These weights can be adjusted in conjunction with medical experts. Path variables can contribute from 0 to 1600 towards the surgical operation risk. The total surgical operation risk score can vary from 0 to 2200.

In the Post Surgery Risk Group the peripheral variables used to calculate the postsurgery risk are tumor type, tumor size, chemotherapy factor, radiotherapy factor, radiation factor, and patient age. All these variables have a weight of 1. As a result, the peripheral variables can contribute anywhere between 0 and 600 towards the post surgery risk. All the path variables except surgery time are used to calculate the post surgery risk. All these variables have a weight of 1. Path variables can contribute from 0 to 500 towards the post surgery risk. The total post surgery risk score can vary from 0 to 1100.

In yet another embodiment, an overall risk factor is calculated. The overall risk factor is the combination of the presurgery, surgery, and post surgery risk factors. The overall risk score can vary between 0 and 5500.

Reasoning With Probability Regions Utilized by Overall Framework

In an embodiment of present invention wherein risk assessment and/or static or dynamic planning are to be engaged in for course of medical treatment involving brain surgery, static planning reasoning mechanism 111, dynamic planning reasoning mechanism 113, and risk assessment reasoning mechanism 117 all utilize an algorithm for uncertainty reasoning. The algorithm for uncertainty reasoning is central to reasoning with brain maps to provide risk assessment. This risk assessment can be static or dynamic and is based on the probability spaces concept. The concept of probability spaces is critical to the surgical navigation algorithm.

Utilizing the probability spaces concept, each grid point of a brain map is defined to have a damage risk associated with it. This damage risk is estimated by how close the grid point is to an eloquence region. Each center of eloquence is assumed to be a source of very high damage risk which outwardly radiates damage risk. Also, a probability space can have a combined risk of two eloquence centers.

Figure 2:
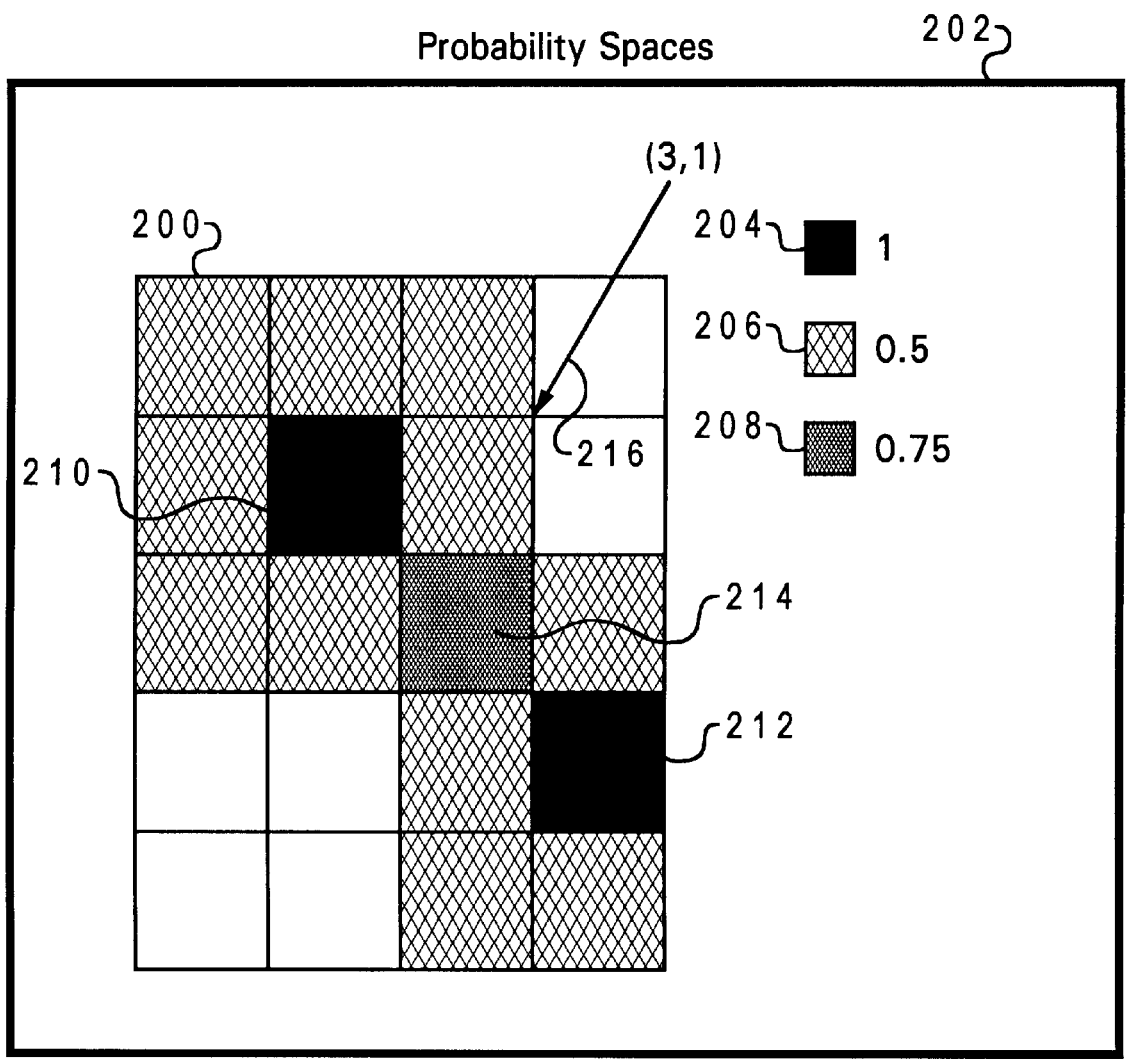
FIG. 2 depicts a two-dimensional illustration of the probability space concept.

Refer now to FIG. 2. FIG. 2 depicts a two-dimensional illustration of the probability space concept. Shown in FIG. 2 is a 4*5 grid 200 of a brain map with a key 202 depicting that black shading is representative of 1.0 probability 204, light shading is representative of 0.5 probability 206, and darker shading is representative of 0.75 probability 208. Depicted are two eloquence centers (dark shaded) 210, 212 having a probability space (damage risk) of 1, and neighboring cells having a probability space of 0.5. One grid cell 214 has a combined probability space of 0.75 (0.5 or 0.5). Also, illustrated in FIG. 2, are rules for combining probabilities. For example, starting at point (3,1) 216 a DOWN, DOWN step sequence has a damage risk of 1 (1 or 0.75); a RIGHT, DOWN step sequence starting at point (3,1) 216 has a damage risk of 0.5 (0 or 0.5). Such calculations are used by the 2D-Step-Score procedure described below.

While the risk calculations herein have been done using probabilistic combination rules for independent variables, embodiments are also envisioned where such risk calculations are based upon heuristically determined formulas when empirical experience dictates that the probabilistic combination rules do not produce acceptable risk assessments.

Planning Surgical Paths in Overall Framework

Planning optimum surgical paths is an activity performed by many embodiments of the present invention. Following are several high-level logic flowcharts descriptive of how an embodiment of the present invention plans these surgical paths For simplicity, these flowcharts will be described as operating in a 2D space; however, those skilled in the art will recognize that the 3D flowcharts are obvious extensions of the 2D flowcharts.

Figure 3:
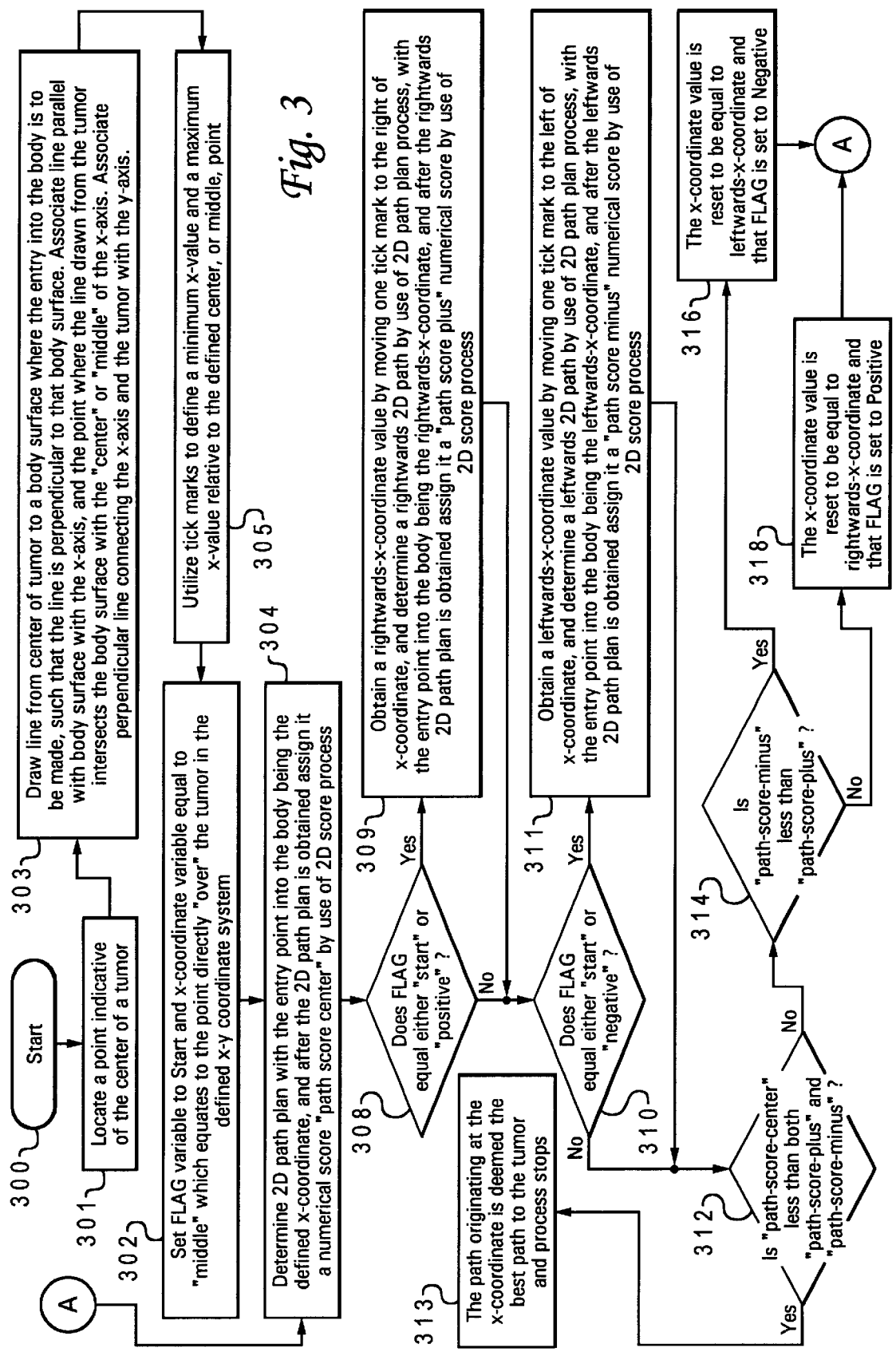
FIG. 3 shows a high-level logic flow chart for 2D static path planning.

Refer now to FIG. 3. FIG. 3 shows a high-level logic flow chart for 2D static path planning. Method step 300 depicts the start of the process. Method step 301 illustrates the location of a point indicative of the center of a tumor as that tumor appears within a brain map. Method step 303 shows that a line is drawn from the tumor to a body surface where the entry into the body is to be made such that the line is perpendicular to that body surface. A line is then posited as running parallel to the body surface and is associated with the x-axis, and the point where the line drawn from the tumor intersects the body surface is thereafter referred to as the "center" or "middle" of the x-axis. Furthermore, the perpendicular line connecting the x-axis and the tumor is known as the y-axis. Method step 305 depicts that thereafter, utilizing tick marks, a minimum x-value and a maximum x-value are defined relative to the center, or middle, point. Thus, method step 301, 303, and method step 305 define an x-y coordinate system relative to the location of the tumor and at least one body surface.

Method step 302 illustrates setting a FLAG variable to Start and an x-coordinate variable equal to "middle" which equates to the point directly "over" the tumor in the defined x-y coordinate system. Method step 304 shows that a 2D path is determined by a 2D path plan process (described below) with the entry point into the body being the defined x-coordinate, and that after the 2D path plan is obtained it is given a numerical "path-score-center" by 2D score process (described below).

Thereafter, method step 308 illustrates that if either FLAG is set to "start" or "positive" then the process proceeds to method step 309 wherein it is shown that a rightwards-x-coordinate value is obtained by incrementing x-coordinate one tick mark, or moving one tick mark to the right of x-coordinate, and a rightwards 2D path is determined by a 2D path plan process (described below) with the entry point into the body being the defined rightwards-x-coordinate, and that after the rightwards 2D path plan is obtained it is given a numerical score, "path-score-plus," by 2D score process (described below).

Thereafter, method step 310 shows that if either FLAG is set to "start" or "negative" then the process proceeds to method step 311 wherein it is shown that a leftwards-x-coordinate value is obtained by decrementing x-coordinate one tick mark, or moving one tick mark to the left of x-coordinate, and a leftwards 2D path is determined by a 2D path plan process (described below) with the entry point into the body being the defined leftwards-x-coordinate, and that after the leftwards 2D path plan is obtained it is given a numerical score, "path-score-minus," by 2D score process (described below).

Subsequently, method step 312 depicts that if "path-score-center" is less than both "path-score-plus" and "path-score_minus" then the process proceeds to method step 313 and stops with the path originating at the point where the x-coordinate was the middle or center is deemed the best path to the tumor. However, in the event that "path-score-center" was not less than both "path-score-plus" and "path-score-minus" then the process proceeds to method step 314 which illustrates the inquiry as to whether "path-score-minus" was less than "path-score-plus."

In the event that "path-score-minus" was less than "path-score-plus," method step 316 shows that the x-coordinate value is reset to be equal to leftwards-x-coordinate and that FLAG is set to Negative; thereafter, the process returns to method step 304 and executes from that point. However, in the event that "path-score-minus" was not less than "path-score-plus," method step 318 depicts that the x-coordinate value is reset to be equal to rightwards-x-coordinate and that FLAG is set to Positive; thereafter, the process returns to method step 304 and executes from that point.

Thus, as shown in the flowchart of FIG. 3, a near optimum path is chosen and is returned as an output.

Figure 4:
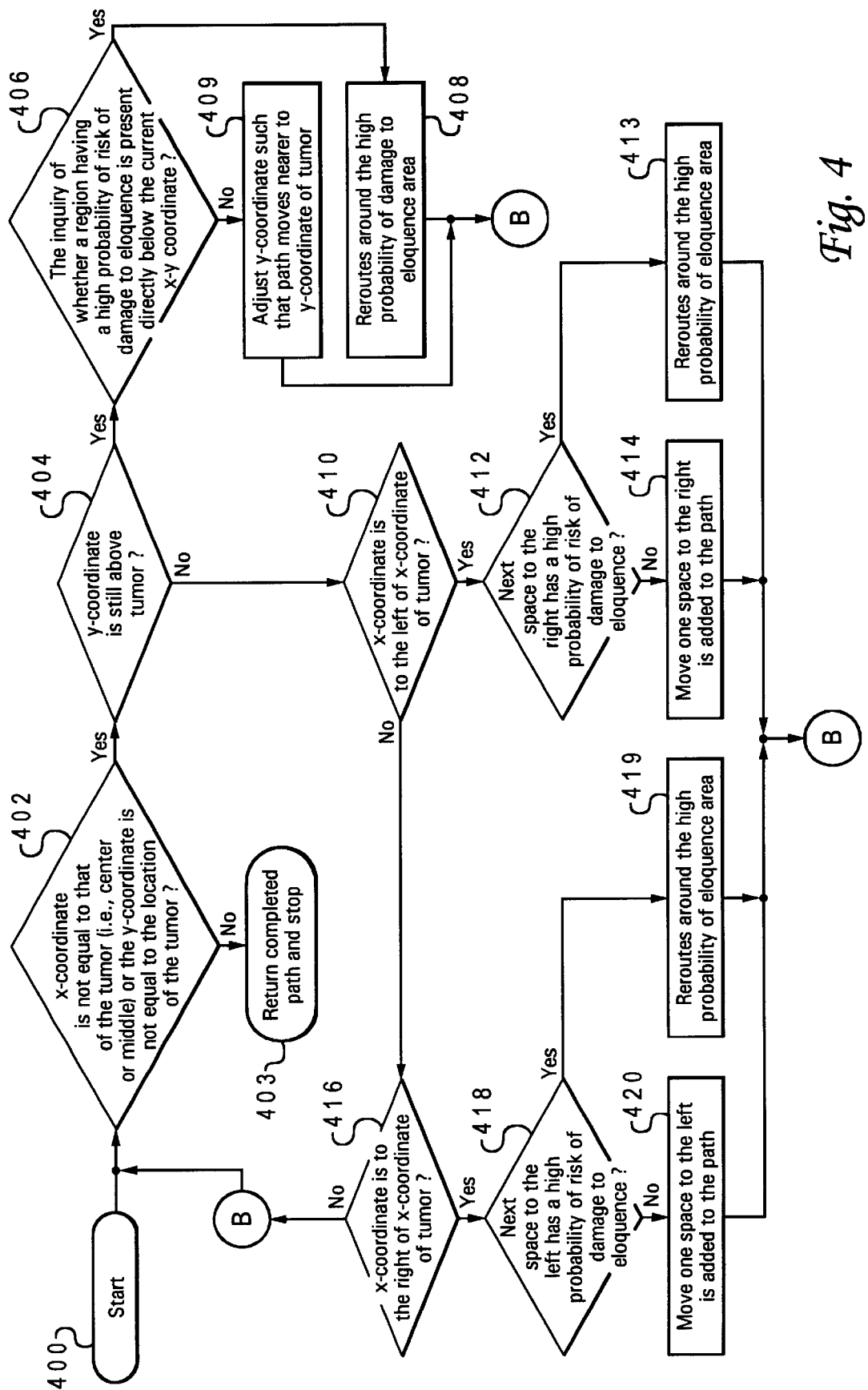
FIG. 4 depicts a high-level logic flow chart for the 2D path plan process.

Refer now to FIG. 4. FIG. 4 depicts a high-level logic flow chart for the 2D path plan process referenced above. In this process, an assumption is made that hook paths are too risky and not allowed and therefore a path cannot go below the y-coordinate of a tumor and come back up. Obviously, all assumptions can be relaxed if no path is found, and such modifications to the process set forth can be achieved by a reasonably skilled programmer. Method step 400 illustrates the start of the process. Method step 402 shows the inquiry of whether x-coordinate is not equal to that of the tumor (i.e., center or middle) or whether the y-coordinate is not equal to the location of the tumor (i.e., the x-y point chosen within the tumor from which a line was drawn to reach a body surface and thus establish an x-y coordinate system relative to the tumor). In the event that either condition shown in method step 402 is true, method step 404 shows that inquiry is made as to whether y-coordinate is still above the y-coordinate of the tumor. If the y-coordinate is above the tumor, then the process proceeds to method step 406 which shows the inquiry of whether a region having a high probability of risk of damage to eloquence is present directly below the current x-y coordinate. In the event that a region having a high probability of risk of damage to eloquence is present directly below the x-y coordinate, method step 408 that the process engages in the 2D reroute path process (described below), and reroutes around the high probability of damage to eloquence area. In the event that a region having a high probability of risk of damage to eloquence is not present directly below the x-y coordinate, method step 409 shows that the y-coordinate is decremented by one tick; that is, is adjusted so that the y-coordinate is now one step nearer the y-coordinate of the tumor. Thereafter, the process returns to method step 402 and re-executes.

If the inquiry of method step 404 shows that y-coordinate is no longer above the y-coordinate of the tumor, the process proceeds to method step 410 which shows the inquiry as to whether x-coordinate is to the left of the x-coordinate of the tumor, in which case the process proceeds to method step 412 which shows the inquiry as to whether the next space to the right has a high probability of risk of damage to eloquence. In the event that the next space to the right has a high probability of risk of damage to eloquence, method step 413 shows that the process engages in the 2D reroute path process (described below), and reroutes around the high probability of damage to eloquence area; however if the next space to the right does not have a high probability of damage to eloquence, method step 414 shows that a move one space to the right is added to the path. Thereafter, the process returns to method step 402 and re-executes.

Thereafter, if the x-coordinate is not to the left of the coordinate of the tumor, method step 416 depicts that the inquiry is made as to whether x-coordinate is to the right of the x-coordinate of the tumor, in which case the process proceeds to method step 418 which shows the inquiry as to whether the next space to the left has a high probability of risk of damage to eloquence. In the event that the next space to the left has a high probability of risk of damage to eloquence, method step 419 shows that the process engages in the 2D reroute path process (described below), and reroutes around the high probability of eloquence area; however if the next space to the left does not have a high probability of damage to eloquence, method step 420 shows that a move one space to the left is added to the path. Thereafter, the process proceeds to method step 402 and reexecutes from that point.

The foregoing described process continues until the inquiry of method step 402 shows that the tumor coordinates have been reached, in which case the process proceeds to method step 402 wherein the complete path is returned and the process stops.

Figure 5:
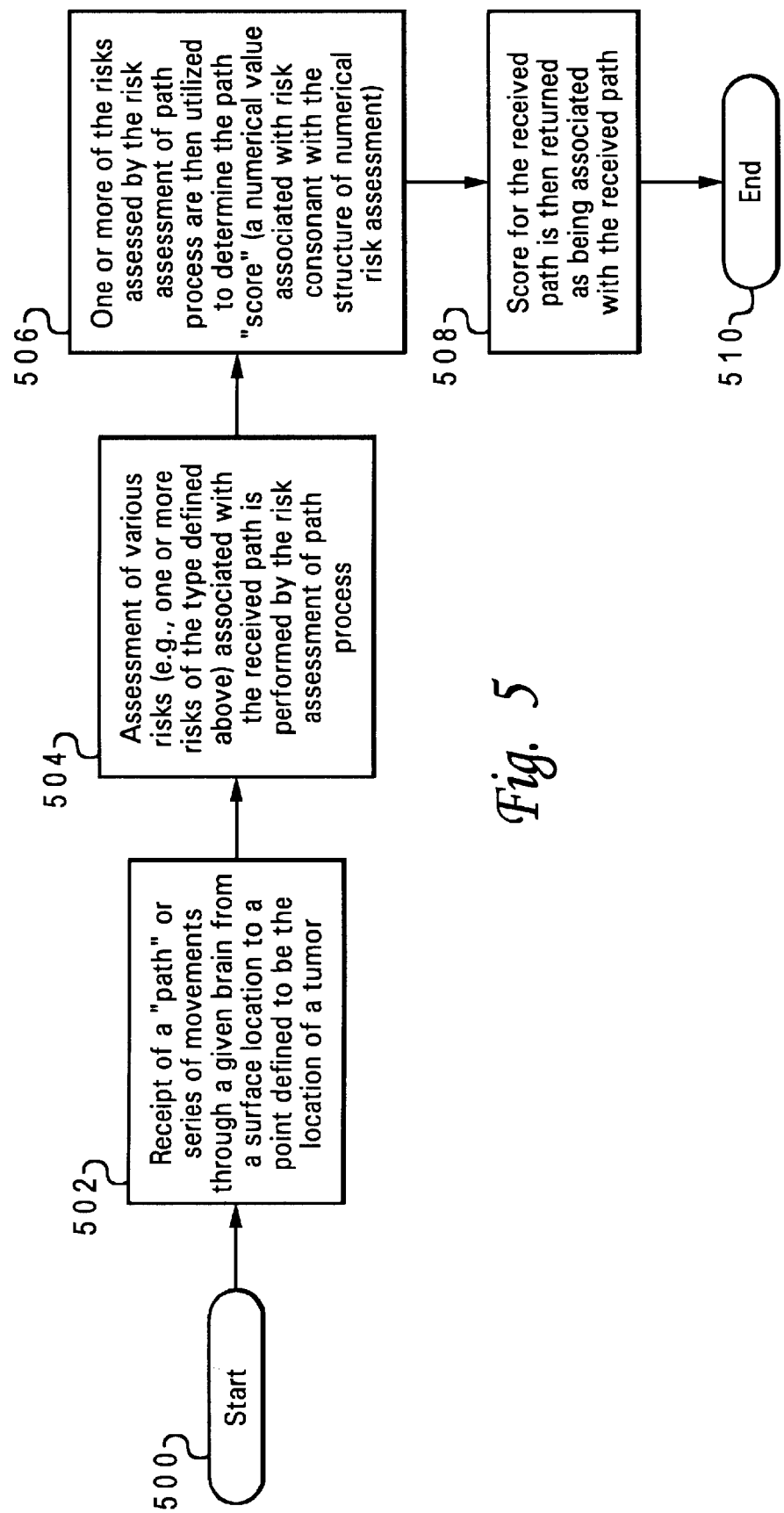
FIG. 5 illustrates the 2D score process.

Refer now to FIG. 5. FIG. 5 illustrates the 2D score process referenced above. Method step 500 shows the start of the process. Method step 502 depicts receipt of a "path" or series of movements through a given brain from a surface location to a point defined to be the location of a tumor. Method step 504 illustrates that assessment of various risks (e.g, one or more risks of the type defined above) associated with the received path is performed by the risk assessment of path process (described below). Method step 506 shows that one or more of the risks assessed by the risk assessment of path process are then utilized to determine the path "score" (or a "raw risk factor," a numerical value associated with risk consonant with the structure of numerical risk assessment discussed above); in one embodiment, this is achieved by setting "score" equal to "total path risk"+"closeness risk"+"eloquent path risk" (1–"removal factor risk")+"eloquent removal risk factor"*10+"surgery time risk"*10), but those skilled in the art will recognize that this is just one among many possible score assessments that could be defined via processes well understood in the art by the system programmer. Method step 508 shows that the score for the received path is then returned as being associated with the received path. Method step 510 shows the end of the process.

Figure 6:
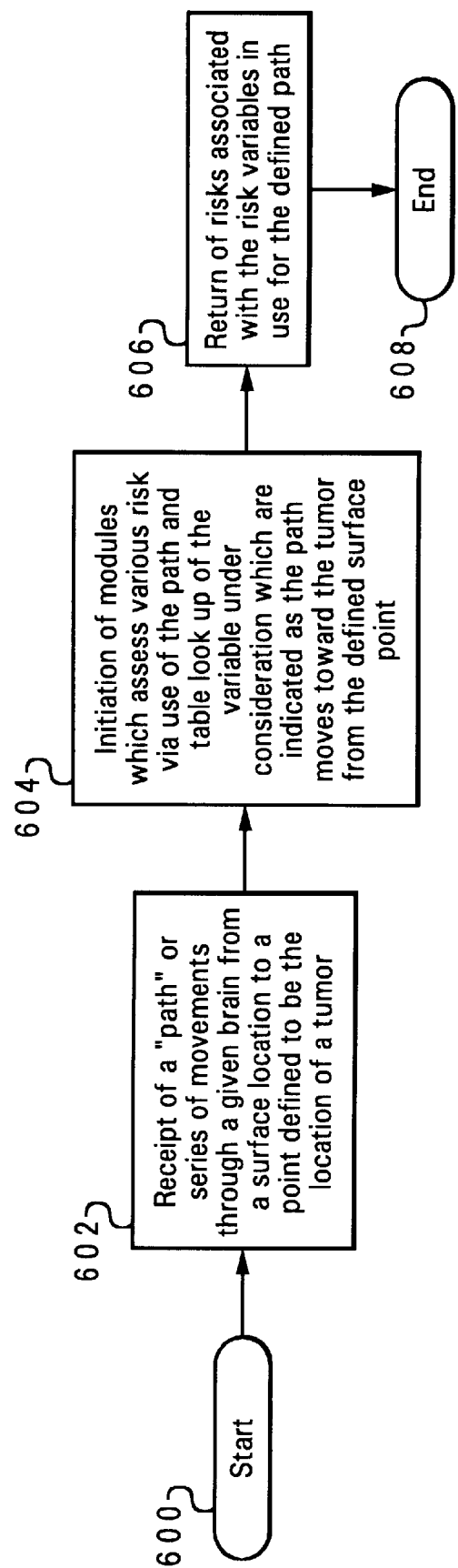
FIG. 6 illustrates the risk assessment of path process.

Refer now to FIG. 6. FIG. 6 illustrates the risk assessment of path process referenced above. The risk assessment of path process which is part of risk assessment mechanism 116 calculates the risk score for each path variable being utilized. This is done by a simple table lookup in a manner well understood by those within the art. Method step 600 shows the start of the process. Method step 602 depicts the receipt of a "path" or series of movements through a given brain from a surface location to a point defined to be the location of a tumor. Method step 604 depicts initiation of modules which assess various risk via use of the path and table look up of the variable under consideration which are indicated as the path moves toward the tumor from the defined surface point; in one embodiment there are subroutines for total path risk, eloquent path risk, tumor removal risk, eloquent removal risk, eloquence closeness risk, and surgery time risk, but those skilled in the art will recognize that such risks are just exemplary and that the systems programmer can use/define more, less, or different risks utilizing the framework of the present invention. Method step 606 shows the return of risks associated with the risk variables in use for the defined path. Method step 608 shows the end of the process.

Figure 7:
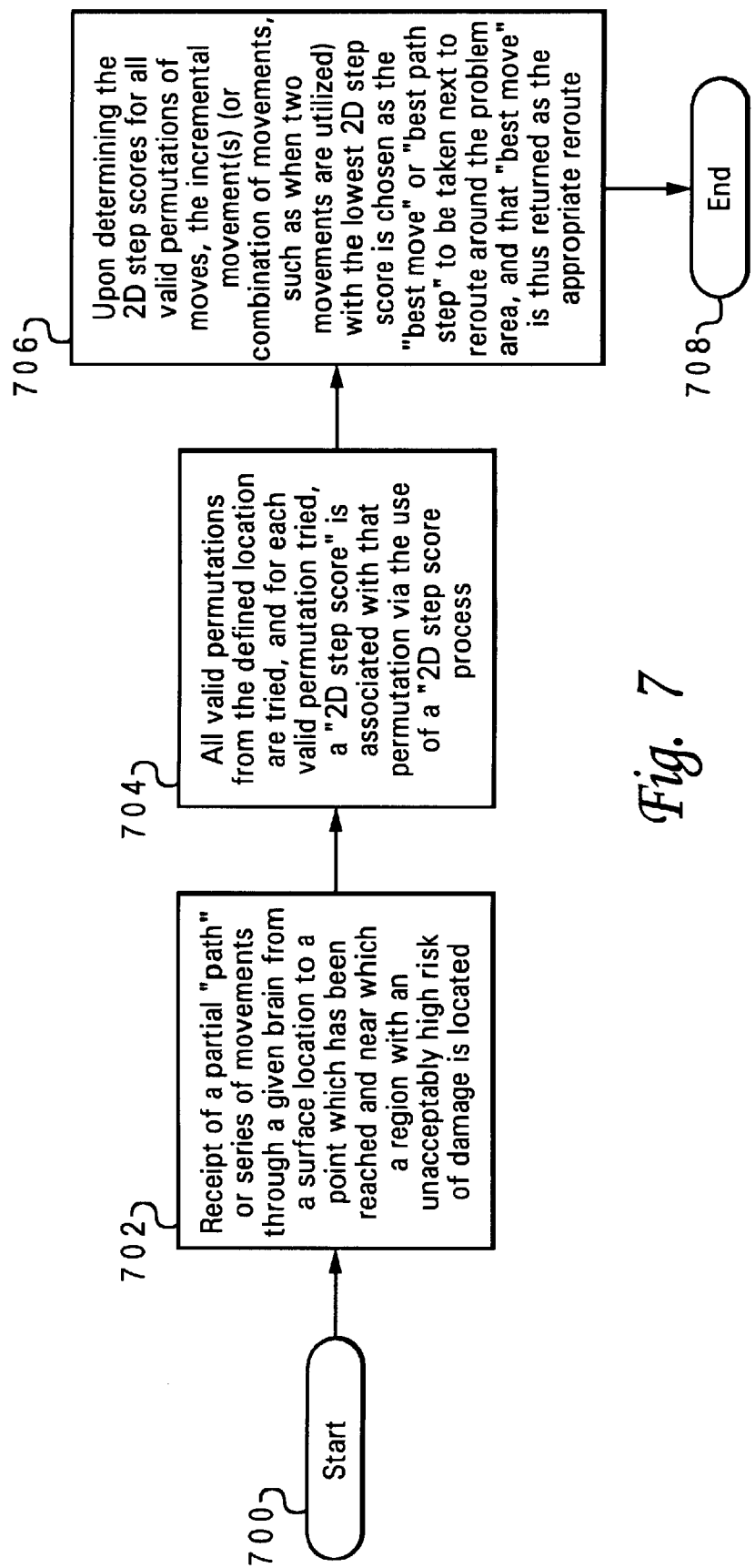
FIG. 7 depicts the 2D reroute path process.

Refer now to FIG. 7. FIG. 7 depicts the 2D reroute path process referenced above. The 2D reroute path procedure calculates the next two least risky steps using probability spaces using the 2D step score procedure (described below) and adds them to the path. It first calculates the step-score exhaustively for all valid possible step sequences. An example of a valid 2-step sequence is DOWN, LEFT. The procedure decides what is a valid permutation. A permutation which has no net result movement like LEFT, RIGHT is not considered a valid permutation.

Method step 700 depicts the start of the process. Method step 702 depicts the receipt of a partial "path" or series of movements through a given brain from a surface location to a point which has been reached and near which a region with an unacceptably high risk of damage is located. Method step 704 shows that all valid permutations from the defined location are tried, and for each valid permutation tried, a "2D step score" is associated with that permutation via the use of a "2D step score process" (described below); in one embodiment, these valid permutations are based upon two incremental movements from a present location, but those skilled in the art will recognize that any number of incremental movements can be utilized. Method step 706 depicts that upon determining the 2D step scores for all valid permutations of moves, the incremental movement (or combination of movements, such as when two movements are utilized) with the lowest "2D step score" is chosen as the "best move" or "best path step" to be taken next to reroute around the problem area, and that "best move" is thus returned as the appropriate reroute. Method step 708 shows the end of the process.

Figure 8:
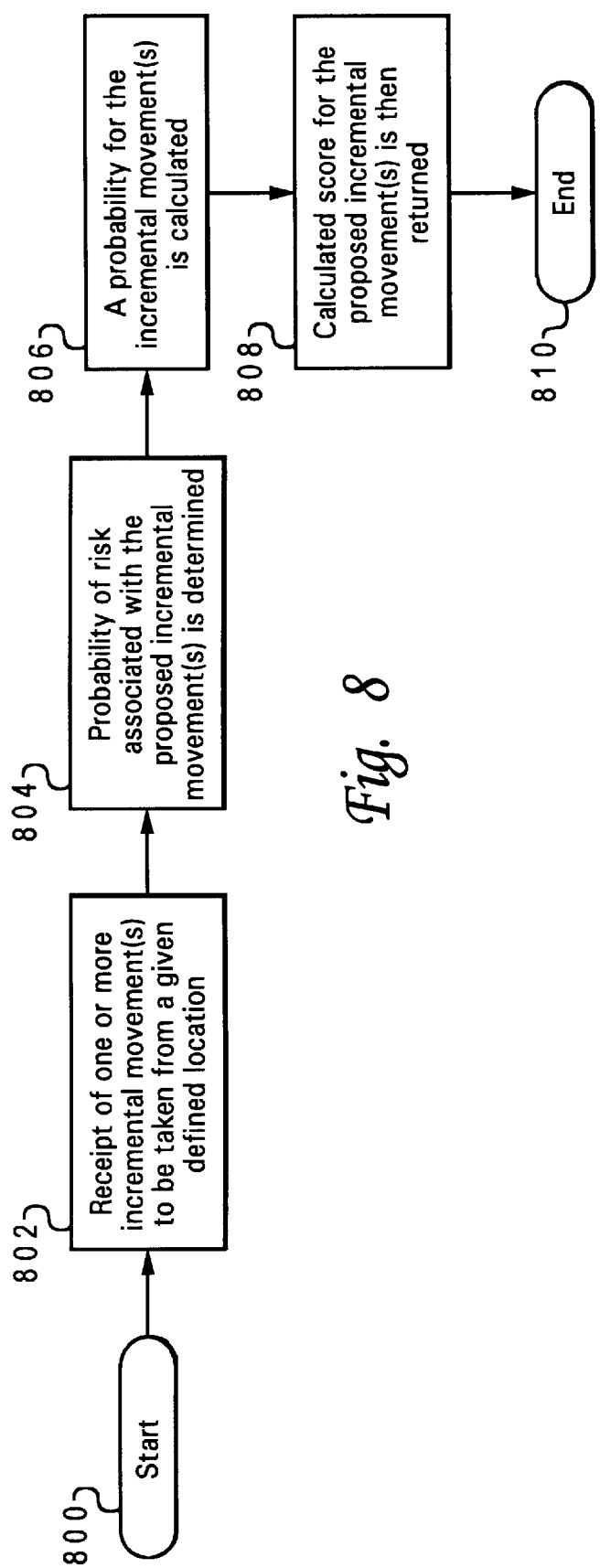
FIG. 8 illustrates the 2D step score process.

Refer now to FIG. 8. FIG. 8 illustrates the 2D step score process referenced above. Method step 800 shows the start of the process. Method step 802 depicts the receipt of one or more incremental movements to be taken from a given defined location; in one embodiment, the number of steps is equal to two, but any number of incremental movements could be proposed. Method step 804 illustrates that the probability of risk associated with each of the proposed incremental movement(s) is determined; in one embodiment, this is the probability associated with each of two incremental movements. Method step 806 depicts that a probability for the incremental movement(s) is calculated; in one embodiment, that probability is a "score" equal to "probability of risk of damage for first move"+"probability of risk of damage for second move"–"probability of risk of damage for first move"*"probability of risk of damage for second move." Method step 808 illustrates that the calculated score for the proposed move(s) is then returned. Method step 810 depicts the end of the process.

Intelligent Neurosurgery Navigation and Assessment Tool

The processes discussed in the flowcharts above can be utilized to provide intelligent neurosurgery navigation and assessment services during presurgery, surgery, and postsurgery. Following are illustrative examples showing how a few, nonexclusive ways, in which such services can be provided. Such examples can be utilized by the systems programmer or knowledge engineer as an aid to understanding the multiple embodiments of the present inventions disclosed herein.

Presurgery Planning

As one example consider using, the static planning mechanism, during presurgery planning to find an optimum or least risky path for tumor removal. The path specified starts at the skull and ends at the tumor face. The determination of this path depends upon the risk assessment using probability spaces. Once a path is chosen a presurgery risk factor is calculated by adding up all the risk factors associated with both path and peripheral variables.

Table 1 shows an example of presurgery planning path variable risk factors. The total score is 520, given a peripheral variable score of 340. Path variables have at least a weight of 2. The closeness to eloquence and eloquent paths have a weight of 3, while the eloquent removal factor has a weight of 4. The foregoing specified weights and values are exemplary and those skilled in the art will recognize that other values and weights can be chosen in accordance with the spirit of the inventions disclosed herein.

TABLE 1

Example Presurgery Risk Score
Total Score = 180 + 340 = 520

| Variable | Value | Risk-Score |
|---|---|---|
| Total Path | Short = 7 | 20 |
| Closeness to Eloquence | 0 | 0 |
| Eloquent Path | 0 | 0 |
| Tumor Removal | 80% | 50 |

TABLE 1-continued

Example Presurgery Risk Score
Total Score = 180 + 340 = 520

| Variable | Value | Risk-Score |
| --- | --- | --- |
| Eloquent Removal | 0% | 0 |
| Surgery Time | 7 steps, 1 bend | 20 |

Artificially Intelligent Surgical Aid for Near-Real-Time Use

The processes disclosed in the above and following flowcharts can also be utilized to produce an artificially intelligent surgical aid to be used in real time during surgery. The primary use during surgery is to calculate the next least risky step given a surgeon request. It can also calculate the next two least risky steps given a surgeon request. Furthermore, it is envisioned that such risky and next risky steps can be predicated on certain defined "resolutions" or specified "path perspectives." For example, a local path perspective would utilize the standard spaces with the defined risks of damage probability, while the intermediate path perspective would create "groups" of spaces having defined risks of damage and assign an overall risk of damage to the group, while the global path perspective would define "groups" even larger than the intermediate groups, and define an overall probability to such defined groups dependent upon the probability of the spaces contained within the larger defined groups. Thereafter, such groups would be utilized "as if" they were the smaller groups, meaning risk assessment, navigation, etc. would be done as normal except that the larger defined groups will be treated and utilized as the smaller regions are normally utilized. Thus, the surgeon can get a next-best-move assessment of at least three different levels of resolution. The calculation of risk is based on the probability space concept.

Figure 9:
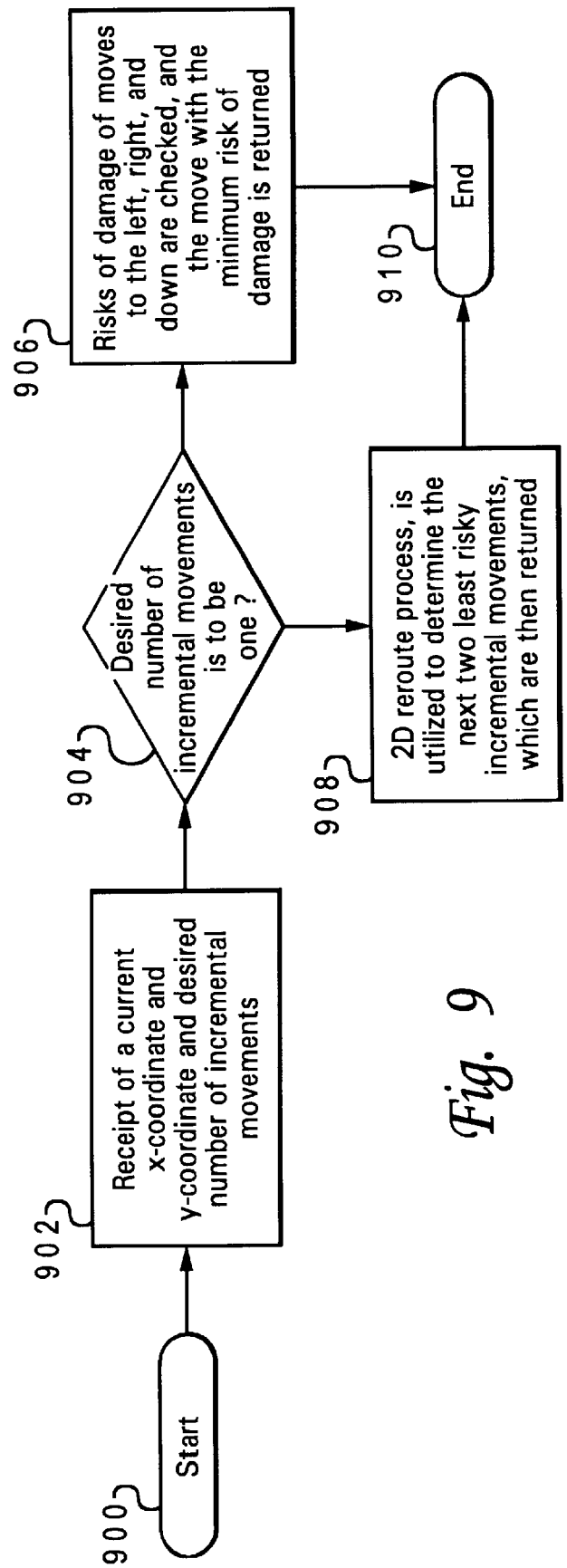
FIG. 9 shows a 2D dynamic path plan procedure.

Refer now to FIG. 9. FIG. 9 shows a 2D dynamic path plan procedure which, in one embodiment returns the least risky next step or the least risky two-step sequence. The 2D dynamic path plan procedure uses the 2D reroute path process to get the 2-step sequence. Also, the risk score associated with surgery is usually the same or similar to the presurgery score. The risk score associated with surgery changes if manual path changes or overrides are made by the surgeon using the procedure below. As an example, if no changes to the presurgery path were made during surgery the surgery risk score from Table 1 would be 520.

Method step 900 depicts the start of the process. Method step 902 illustrates the receipt of a current x-coordinate and y-coordinate and desired number of incremental movements; while the desired number of incremental movements could be any size, in one embodiment the number of incremental movements can be specified to be one or two incremental movements. Method step 904 depicts the inquiry as to whether the desired number of incremental movements is to be one. In the event that the desired number of incremental movements is to be one, then the process proceeds to method step 906 which depicts that the risks of damage of moves to the left, right, and down are checked, and that the move with the minimum risk of damage is returned.

In the event that the desired number of incremental movements is two, the process proceeds to method step 908 which shows that the 2D reroute process, described above, is utilized to determine the next two least risky incremental movements, which are then returned. Method step 910 depicts the end of the process.

It has been discussed above that computer-aided localizing and guidance devices have been devised. These include stereotactic guidance systems, real-time imaging, and computer guided mechanical arms. In this environment, the disclosed intelligent system can be incorporated into such systems to help with planned navigating and also with a real-time risk assessment of a surgical operation should changes to the plan be deemed necessary, which will enhance the utility of these guidance systems and ultimately the neurosurgery's result. Furthermore, in addition to the foregoing, it will be recognized by those within the art that the 2D static plain process described above could be utilized at a point within surgery to calculate and display (as on a CRT or other display device) paths associated with the least risky path to a tumor from a given location within the brain. Furthermore, the different resolutions could be utilized to generate paths with minimum risks dependent upon perspective.

Postsurgery Prognosis

As another example, consider using the static planning mechanism during postsurgery planning. The post surgery prognosis can be provided by using risk assessment mechanism 116. The postsurgery risk factor is calculated by adding up all the risk factors associated with the relevant peripheral and path variables. These relevant peripheral variables are tumor type, tumor size, chemotherapy factor, radiotherapy factor, radiation factor, and patient age. The relevant path variables are tumor removal factor, total path, eloquent path, closeness to eloquence, and eloquent removal factor.

Table 2 below shows an example post surgery risk score and its contributing factors as would be calculated in one embodiment of the present invention. The total score in this example is 460.

TABLE 2

Example Post Surgery Risk Score
Total Score = 460

| Variable | Value | Risk-Score |
| --- | --- | --- |
| Tumor Type | Aristocytoma Grade II | 50 |
| Tumor Size | Medium | 50 |
| Chemotherapy | Non Responsive | 100 |
| Radiotherapy | Mid Responsive | 50 |
| Radiation | Responsive | 20 |
| Patient Age | 55 | 100 |
| Tumor Removal | 80% | 50 |
| Total Path | Short | 20 |
| Eloquent Path | 0% | 0 |
| Eloquence Closeness | 20% | 20 |
| Eloquent Removal | 0% | 0 |

Navigation example

Figure 10:
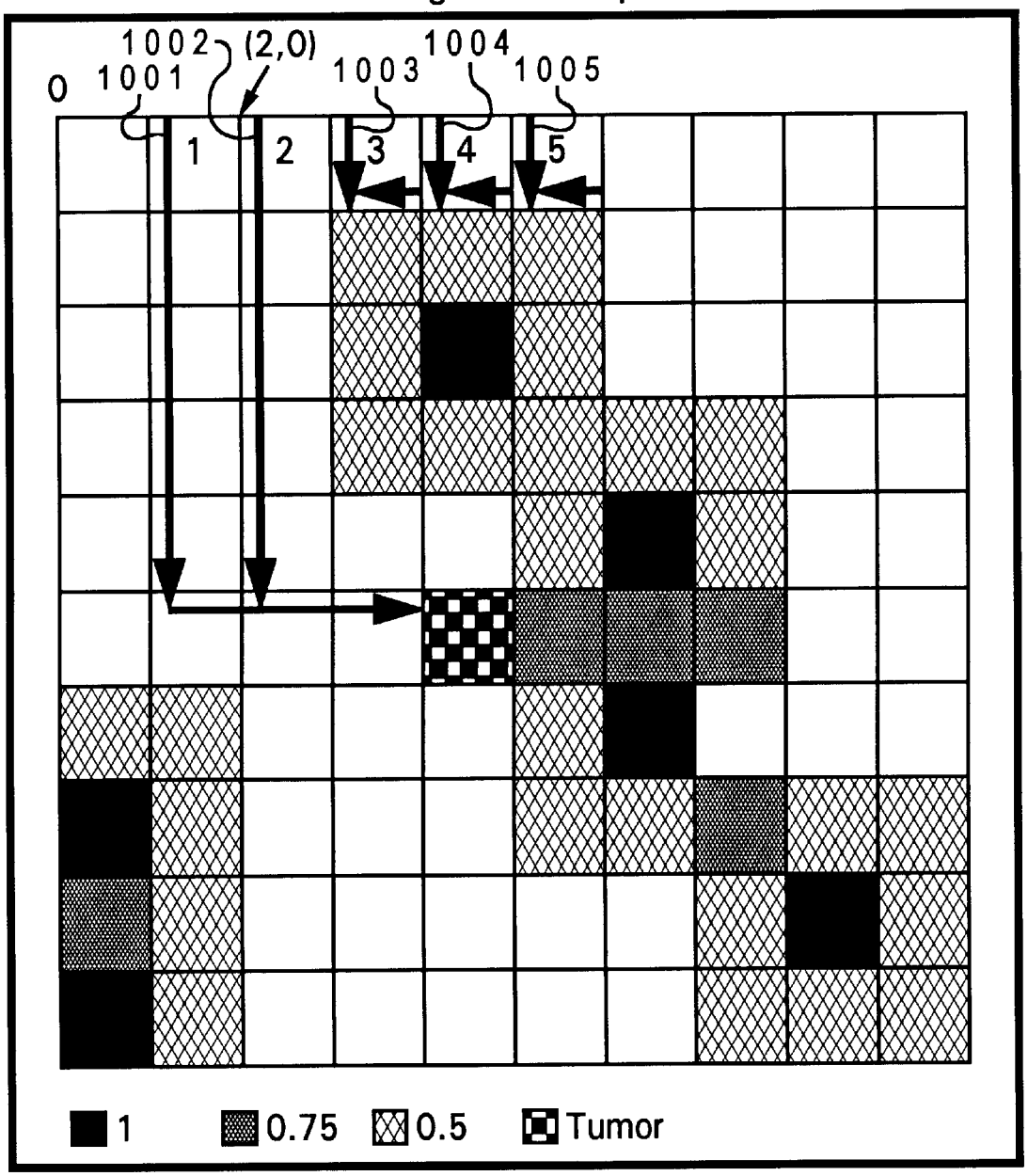
FIG. 10 shows an example of a different paths through a 10×10 grid to a tumor located at coordinate (4,5) within the grid.

Refer now to FIG. 10. FIG. 10 shows an example of a 10×10 grid where the tumor is located at coordinate (4,5). The eloquence regions are marked by the light and dark grey shaded areas. The 2D static plan path process tries paths starting from (4,0) down to (1,0). The path from (5,0) and higher are not pursued. These five paths 1001, 1002, 1003, 1004, 1005 are shown in FIG. 10.

Table 3 shows the raw risk factors associated with all five paths 1001, 1002, 1003, 1004, 1005 and the total raw risk factor score used to choose the least risky path. Based on the scores shown in Table 3, the path from (2,0) is chosen. Once this path is chosen the risk assessment path procedure, in the fashion discussed above, calculates the risk factors using lookup tables associated with the path variables of this path. Table 4 shows these risk factor scores for path variables.

TABLE 3

Navigation Path Raw Scores
Best Raw Score = 170

| Path | Total Path | Closeness | Eloquent Path | Tumor Removal | Eloquent Removal | Time | Raw Risk |
|---|---|---|---|---|---|---|---|
| 1 | 8 | 0 | 0 | 80 | 0 | 8t + 1b | 190 |
| 2 | 7 | 0 | 0 | 80 | 0 | 7t + 1b | 170 |
| 3 | 8 | 1 | 0 | 80 | 0 | 8t + 3b | 220 |
| 4 | 9 | 2 | 0 | 80 | 0 | 9t + 3b | 250 |
| 5 | 10 | 3 | 0 | 80 | 0 | 10t + 3b | 280 |

TABLE 4

Path Variables Risk Score
Total Path Variable Risk Score = 180

| Variable | Value | Risk-Score |
|---|---|---|
| Total Path | Short = 7 | 20 |
| Closeness to Eloquence | 0 | 0 |
| Eloquent Path | 0 | 0 |
| Tumor Removal | 80% | 50 |
| Eloquent Removal | 0% | 0 |
| Surgery Time | 7 steps, 1 bend | 20 |

As has been discussed, the artificially intelligent style mechanisms disclosed above can be used during presurgery planning, surgery, and post surgery prognosis.

The tools disclosed herein can be used in conjunction with neurosurgery guidance tools. The development of such intelligent risk assessment and navigation tools should prove to be beneficial for the improvement of neurosurgery. These tools should enhance a neurosurgery guidance tool and reduce the risk of neurosurgery.

Figure 11:
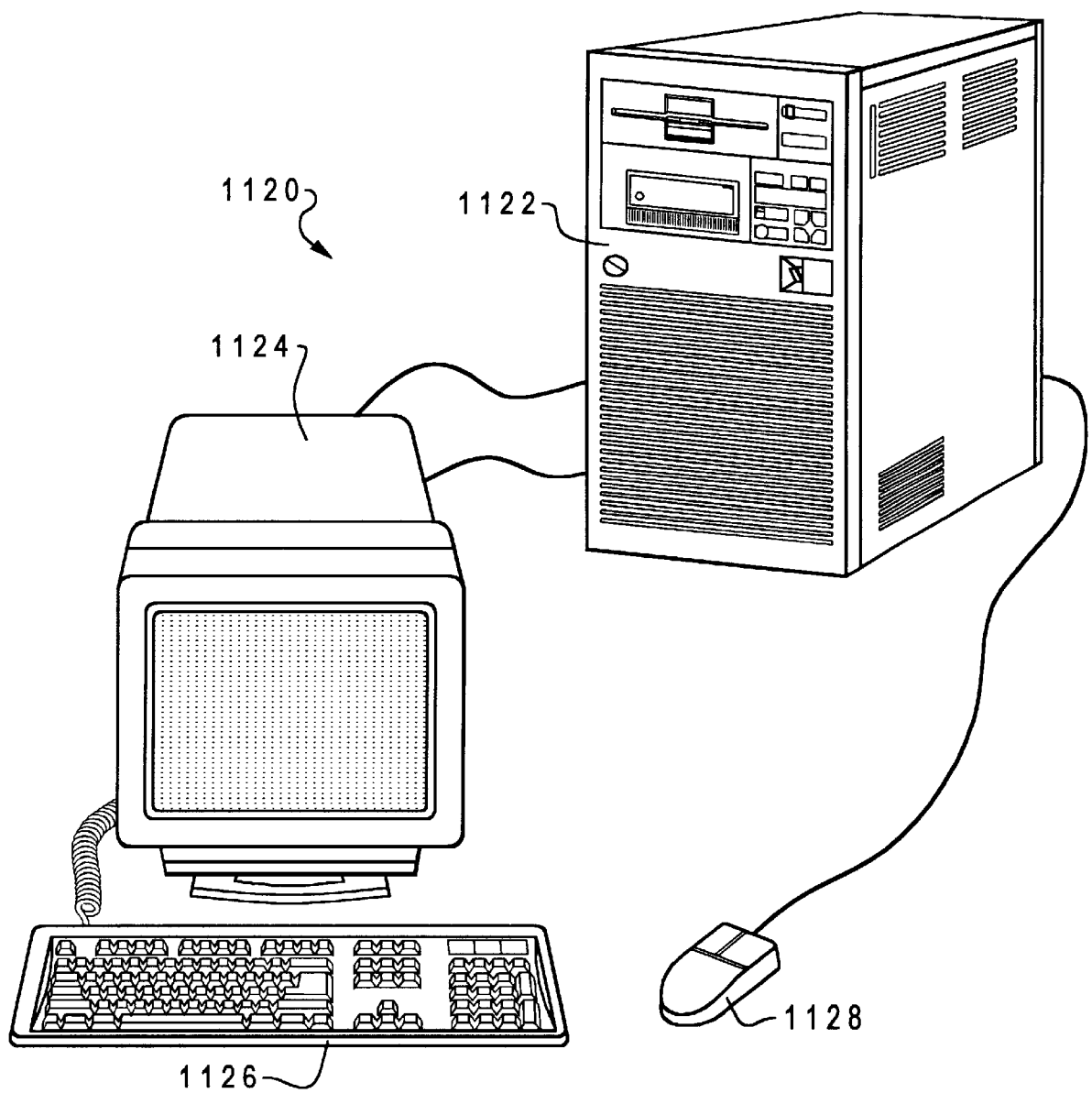
FIG. 11 depicts a pictorial representation of a data-processing system which can be utilized in accordance with the method and system of an illustrative embodiment of the present invention.

With reference now to the figures and in particular with reference now to FIG. 11, there is depicted a pictorial representation of a data-processing system which can be utilized in accordance with the method and system of an illustrative embodiment of the present invention. The method and system provided by an illustrative embodiment of the present invention can be implemented with the data-processing system depicted in FIG. 11. A computer 1120 is depicted which includes a system unit 1122, a video display terminal 1124, a keyboard 1126, and a mouse 1128. Computer 1120 may be implemented utilizing any suitably powerful computer, such as commercially available mainframe computers, minicomputers, or microcomputers.

Figure 12:
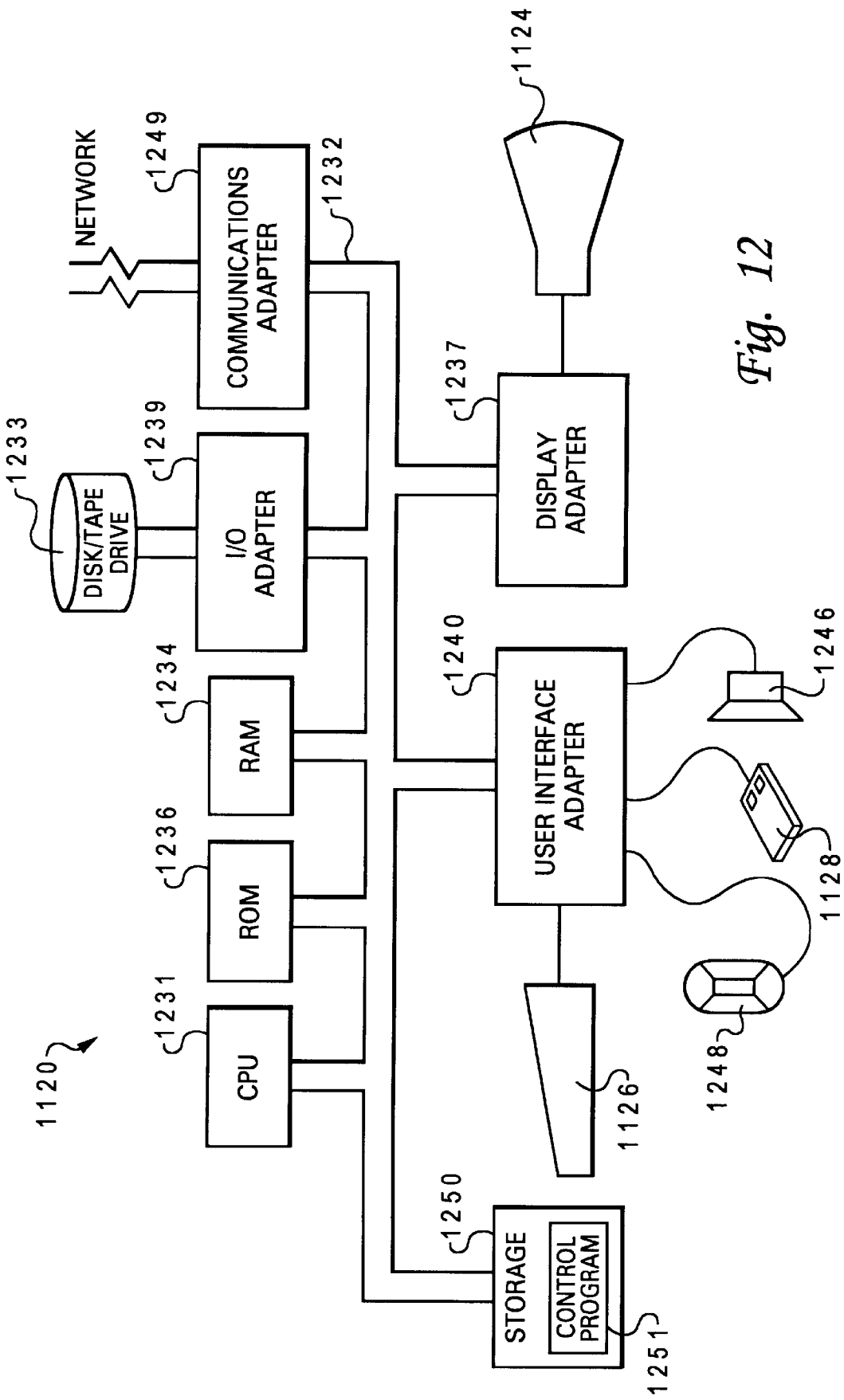
FIG. 12 illustrates a representative environment which can be utilized in accordance with the method and system of an illustrative embodiment of the present invention.

FIG. 12 is an illustration of a representative hardware environment which can be utilized in accordance with the method and system of an illustrative embodiment of the present invention. FIG. 12 depicts selected components in computer 1120 in which an illustrative embodiment of the present invention may be implemented. System unit 1122 includes a Central Processing Unit ("CPU") 1231, such as a conventional microprocessor, and a number of other units interconnected via system bus 1232. Computer 1120 includes random-access memory ("RAM") 1234, read-only memory ("ROM") 1236, display adapter 1237 for connecting system bus 1232 to video display terminal 1124, and I/O adapter 1239 for connecting peripheral devices (e.g., disk and tape drives 1233) to system bus 1232. Video display terminal 1124 is the visual output of computer 1120, which can be a CRT-based video display well-known in the art of computer hardware. However, with a portable or notebook-based computer, video display terminal 1124 can be replaced with an LCD-based or a gas plasma-based flat-panel display. Computer 1120 further includes user interface adapter 1240 for connecting keyboard 1126, mouse 1128, speaker 1246, microphone 1248, and/or other user interface devices, such as a touch screen device (not shown), to system bus 1232. Communications adapter 1249 connects computer 1120 to a data-processing network.

Any suitable machine-readable media may retain the method and system of an illustrative embodiment of the present invention, such as RAM 1234, ROM 1236, a magnetic diskette, magnetic tape, or optical disk (the last three being located in disk and tape drives 1233). Any suitable operating system and associated graphical user interface (e.g., Microsoft Windows) may direct CPU 1231. For example, the AIX operating system and AIXwindows windowing system (i.e., graphical user interface) can direct CPU 1231. The AIX operating system is IBM's implementation of the UNIX operating system. UNIX is a trademark of UNIX Systems Laboratories, Inc. The RISC System/6000 system, among others, can run on the AIX operating system. Other technologies can also be utilized in conjunction with CPU 1231, such as touch-screen technology or human voice control. In addition, computer 1120 includes a control program 1151 which resides within computer storage 1250. Control program 1251 contains instructions that when executed on CPU 1231 carries out one or more of the operations depicted in the logic flowcharts of FIGS. 3, 4, 5, 6, 7, 8, 9, and one or more of the associated operations depicted in schematic diagrams of FIGS. 1, 2, and 10 or any other illustrative example as described herein.

Those skilled in the art will appreciate that the hardware depicted in FIG. 12 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already depicted.

As a final matter, it is important that while an illustrative embodiment of the present invention has been, and will continue to be, described in the context of a fully functional computing system, those skilled in the art will appreciate that the mechanisms of an illustrative embodiment of the present invention are capable of being distributed as a program product in a variety of forms, and that an illustrative embodiment of the present invention applies equally regardless of the particular type of signal bearing media used to actually carry out the distribution. Examples of signal bearing media include recordable type media such as floppy disks, hard disk drives, CD ROMs, and transmission type media such as digital and analogue communication links.

While the invention has been shown and described with reference to particular embodiments thereof, it will be understood by those skilled in the art that the foregoing and other changes in form and detail may be made therein without departing from the spirit and scope of the invention, which is defined by the following claims.

I claim:

1. A method for providing artificial intelligence for planning optimum surgical paths to a tumor in an organ, said artificial intelligence to be provided by a data-processing system programmed to achieve said method, and said method comprising the steps of:

defining one or more risk-of-damage probability spaces which associate a risk-of-damage probability with a region within an organ; and in response to said step of defining, calculating an optimum path to a tumor in an organ.

2. The method of claim 1, wherein said step of defining risk-of-damage probability spaces further includes the steps of:
   defining at least one functional region within an organ;
   subdividing the at least one functional region into one or more subregions; and
   associating a risk-of-damage probability with each of the one or more subregions such that a higher probability indicates a concomitant loss of function of the at least one functional area within the organ.

3. The method of claim 2, wherein said step of calculating an optimum path to a tumor in an organ further includes the steps of:
   defining an entry point; and
   determining an optimal path to the tumor in the organ from the entry point.

4. The method of claim 3, wherein said step of determining an optimal path to the tumor in the organ from the entry point further includes the steps of:
   defining an initial position to be the entry point;
   determining the location of the tumor in the organ relative to the initial position;
   positing a first incremental movement, relative to the initial position, toward the tumor in the organ;
   calculating a risk-of-damage for the first incremental movement based upon the risk-of-damage probability associated with each of the one or more subregions that would be intersected by the first incremental movement toward the tumor;
   if the risk-of-damage for the first incremental movement toward the tumor is acceptable, then
   saving the first incremental movement as a valid path movement, and defining the initial position to be the position reached upon execution of the first incremental movement, but
   the risk-of-damage for the first incremental movement is unacceptable, then,
   positing a second incremental movement such that a surgical instrument is rerouted, relative to the initial position, away from the one or more subregions that would be intersected by the first incremental movement and toward the tumor in the organ,
   calculating a risk-of-damage for the second incremental movement based upon the risk-of-damage probability associated with each of the one or more subregions that would be intersected by the second incremental movement toward the tumor,
   if the risk-of damage for the second incremental movement is acceptable, then,
   saving the second incremental movement as a valid path movement, and defining the initial position to be the position reached upon execution of the second incremental movement, but if the risk-of-damage for the second incremental movement is unacceptable, then, defining the first incremental movement to be the second incremental movement, and
   reengaging in said calculating a risk-of-damage for the first incremental movement and said step conditioned upon the risk-of-damage for the initial incremental movement toward the tumor;
   if the last valid path movement saved intersects the tumor in the organ, then calculating a risk-of-damage associated with the path from the defined entry point to the tumor formed by the saved valid path movements, but if the last valid path movement saved does not intersect the tumor in the organ, then
   redefining the initial position to be the position reached upon the execution of the last valid path movement saved, and
   reengaging in said step of determining the location of the tumor in the organ relative to the initial position, said step of positing a first incremental movement, relative to the initial position, toward the tumor in the organ, said step of calculating a risk-of-damage for the first incremental movement, and said step conditioned upon the risk-of-damage for the first incremental movement toward the tumor.

5. The method of claim 3, further comprising the steps of:
   defining an increment;
   defining a second entry point to be the entry point modified by the increment; and
   redefining the entry point to be the second entry point.

6. The method of claim 1, wherein said step of defining risk-of-damage probability spaces within an organ further includes the step of defining risk-of-damage probability spaces within a brain.

7. The method of claim 6, wherein said step of calculating an optimum path to a tumor in an organ further includes the step of calculating an optimum path to a tumor in a brain.

8. A system for providing artificial intelligence for planning optimum surgical paths to a tumor in an organ, said artificial intelligence to be provided by a data-processing system programmed to achieve said planning, said system comprising:
   means for defining one or more risk-of-damage probability spaces which associate a risk-of-damage probability with a region within an organ; and
   means, responsive to said step of defining, for calculating an optimum path to a tumor in an organ.

9. The system of claim 8, wherein said means for defining risk-of-damage probability spaces further includes:
   means for defining at least one functional region within an organ;
   means for subdividing the at least one functional region into one or more subregions; and
   means for associating a risk-of-damage probability with each of the one or more subregions such that a higher probability indicates a concomitant loss of function of the at least one functional area within the organ.

10. The system of claim 9, wherein said means for calculating an optimum path to a tumor in an organ further includes:
    means for defining an entry point; and
    means for determining an optimal path to the tumor in the organ from the entry point.

11. The system of claim 10, wherein said means for determining an optimal path to the tumor in the organ from the entry point further includes:
    means for defining an initial position to be the entry point;
    means for determining the location of the tumor in the organ relative to the initial position;
    means for positing a first incremental movement, relative to the initial position, toward the tumor in the organ;
    means for calculating a risk-of-damage for the first incremental movement based upon the risk-of-damage probability associated with each of the one or more subregions that would be intersected by the first incremental movement toward the tumor;

means for, if the risk-of-damage for the first incremental movement toward the tumor is acceptable, then saving the first incremental movement as a valid path movement, and defining the initial position to be the position reached upon execution of the first incremental movement, but if the risk-of-damage for the first incremental movement is unacceptable, then, positing a second incremental movement such that a surgical instrument is rerouted, relative to the initial position, away from the one or more subregions that would be intersected by the first incremental movement and toward the tumor in the organ, and calculating a risk-of-damage for the second incremental movement based upon the risk-of-damage probability associated with each of the one or more subregions that would be intersected by the second incremental movement toward the tumor, if the risk-of damage for the second incremental movement is acceptable, then, saving the second incremental movement as a valid path movement, and defining the initial position to be the position reached upon execution of the second incremental movement, but if the risk-of-damage for the second incremental movement is unacceptable, then, defining the first incremental movement to be the second incremental movement, and reengaging in said means for calculating a risk-of-damage for the first incremental movement and said means conditioned upon the risk-of-damage for the initial incremental movement toward the tumor;

means for, if the last valid path movement saved intersects the tumor in the organ, then calculating a risk-of-damage associated with the path from the defined entry point to the tumor formed by the saved valid path movements, but if the last valid path movement saved does not intersect the tumor in the organ, then redefining the initial position to be the position reached upon the execution of the last valid path movement saved, and reengaging said means for determining the location of the tumor in the organ relative to the initial position, said means for positing a first incremental movement, relative to the initial position, toward the tumor in the organ, said means for calculating a risk-of-damage for the first incremental movement, and said means conditioned upon the risk-of-damage for the first incremental movement toward the tumor.

12. The system of claim 10, further comprising:

means for defining an increment;

means for defining a second entry point to be the entry point modified by the increment; and means for redefining the entry point to be the second entry point.

13. The system of claim 8, wherein said means for defining risk-of-damage probability spaces within an organ further includes means for defining risk-of-damage probability spaces within a brain.

14. The system of claim 13, wherein said means for calculating an optimum path to a tumor in an organ further includes means for calculating an optimum path to a tumor in a brain.

15. A method for providing artificial intelligence for minimizing risk during a surgical procedure, said artificial intelligence to be provided by a data-processing system programmed to achieve said method, said method comprising the steps of:

defining one or more risk-of-damage probability spaces which associate a risk-of-damage Probability with a region within an organ;

receiving an input of a location, relative to the organ, of a surgical instrument;

receiving an input of a location of a tumor within the organ;

defining one or more moves relative to one or more paths, defined by one or more specified path perspectives, from the location of the surgical instrument to the tumor within the organ;

assessing one or more risks for the defined one or more moves relative to the one or more paths defined by one or more specified path perspectives; and indicating the risks associated with the one or more moves relative to the one or more paths defined by one or more specified path perspectives.

16. The method of claim 15, wherein said step of defining risk-of-damage probability spaces further includes the steps of:

defining at least one functional region within an organ;

subdividing the at least one functional region into one or more subregions; and assigning risk-of-damage to the one or more subregions such that a higher probability indicates a concomitant loss of function of the at least one functional area within the organ.

17. The method of claim 15, wherein said step of defining one or more moves further comprises the step of defining one or more incremental movements relative to the location of the surgical instrument.

18. The method of claim 17, wherein said step of assessing one or more risks for the defined one or more moves relative to one or more defined paths further comprises the steps of:

specifying one or more path perspectives;

in response to said step of specifying one or more path perspectives, creating groups of said defined one or more risk-of-damage probability spaces appropriate to said specified one or more path perspectives;

calculating the risks of the defined one or more moves relative to each of the one or more paths based upon the one or more created groups of said defined one or more risk-of-damage probability spaces intersected by the one or more paths.

19. The method of claim 18, wherein said step of specifying one or more path perspectives further includes the step of specifying a local path perspective which utilizes standard spaces with defined risk-of-damage probability.

20. The method of claim 18, wherein said step of specifying one or more path perspectives further includes the step of specifying an intermediate path perspective which groups spaces with defined risk-of-damage probabilities.

21. The method of claim 18, wherein said step of specifying one or more path perspectives further includes the step of specifying a global path perspective which groups spaces with defined risk-of-damage probabilities.

22. A system for providing artificial intelligence for minimizing risk during a surgical procedure, said artificial intelligence to be provided by a data-processing system programmed to achieve said risk minimization, said system comprising:

means for defining one or more risk-of-damage probability spaces which associate a risk-of-damage probability with a region within an organ;

means for receiving an input of a location, relative to the organ, of a surgical instrument;

means for receiving an input of a location of a tumor within the organ;

means for defining one or more moves relative to one or more paths, defined by one or more specified path perspectives, from the location of the surgical instrument to the tumor within the organ;

means for assessing one or more risks for the defined one or more moves relative to the one or more paths defined by one or more specified path perspectives; and means for indicating the risks associated with the one or more moves relative to the one or more paths defined by one or more specified path perspectives.

23. The system of claim 22, wherein said means for defining risk-of-damage probability spaces further includes:

means for defining at least one functional region within an organ;

means for subdividing the at least one functional region into one or more subregions; and means for assigning risk-of-damage to the one or more subregions such that a higher probability indicates a concomitant loss of function of the at least one functional area within the organ.

24. The system of claim 22, wherein said means for defining one or more moves further comprises means for defining one or more incremental movements relative to the location of the surgical instrument.

25. The system of claim 24, wherein said means for assessing one or more risks for the defined one or more moves relative to one or more defined paths further comprises:

means for specifying one or more path perspectives;

means, responsive to said step of specifying one or more path perspectives, for creating groups of said defined one or more risk-of-damage probability spaces appropriate to said specified one or more path perspectives;

means for calculating the risks of the defined one or more moves relative to each of the one or more paths based upon the one or more created groups of said defined one or more risk-of-damage probability spaces intersected by the one or more paths.

26. The system of claim 25, wherein said means for specifying one or more path perspectives further includes means for specifying a local path perspective which utilizes standard spaces with defined risk-of-damage probability.

27. The system of claim 25, wherein said means for specifying one or more path perspectives further includes means for specifying an intermediate path perspective which groups spaces with defined risk-of-damage probabilities.

28. The method of claim 25, wherein said step of specifying one or more path perspectives further includes the step of specifying a global path perspective which groups spaces with defined risk-of-damage probabilities.

* * * * *